United States Patent
Kitt

(10) Patent No.: US 11,911,001 B2
(45) Date of Patent: Feb. 27, 2024

(54) ENDOSCOPE CLIP

(71) Applicant: Keymed (Medical & Industrial Equipment) Limited, Southend-on-Sea (GB)

(72) Inventor: David Kitt, Southend-on-Sea (GB)

(73) Assignee: KEYMED (MEDICAL & INDUSTRIAL EQUIPMENT) LIMITED, Essex (GB)

(*) Notice: Subject to any disclaimer, the term of this patent is extended or adjusted under 35 U.S.C. 154(b) by 55 days.

(21) Appl. No.: 17/533,329

(22) Filed: Nov. 23, 2021

(65) Prior Publication Data

US 2022/0167830 A1 Jun. 2, 2022

(30) Foreign Application Priority Data

Dec. 2, 2020 (GB) .................................. 2018979.1

(51) Int. Cl.
*A61B 1/00* (2006.01)

(52) U.S. Cl.
CPC ........ *A61B 1/0014* (2013.01); *A61B 1/00066* (2013.01); *A61B 1/00142* (2013.01)

(58) Field of Classification Search
CPC .. A61B 1/0014; A61B 1/00142; A61M 25/02; A61M 2502/024; F16B 2/10
See application file for complete search history.

(56) References Cited

U.S. PATENT DOCUMENTS

| | | | | |
|---|---|---|---|---|
| 2,961,479 A * | 11/1960 | Bertling | .................... | H02G 7/12 285/902 |
| 4,029,103 A * | 6/1977 | McConnell | ........... | A61M 25/02 604/179 |
| 4,707,906 A * | 11/1987 | Posey | ..................... | F16L 3/223 24/339 |
| 4,820,274 A * | 4/1989 | Choksi | ................ | A61M 5/1418 604/174 |
| 5,841,003 A * | 11/1998 | Slaugh | .................. | C07C 29/141 568/451 |
| 5,871,189 A * | 2/1999 | Hoftman | .................. | F16L 3/13 248/229.16 |
| 5,884,372 A * | 3/1999 | Anscher | .................... | F16L 3/13 24/339 |
| 6,804,866 B2 * | 10/2004 | Lemke | ............. | A61M 16/0683 604/174 |

(Continued)

FOREIGN PATENT DOCUMENTS

JP 2013-002623 A 1/2013

OTHER PUBLICATIONS

Great Britain Search Report dated May 18, 2021 received in GB2018979.1.

*Primary Examiner* — Matthew J Kasztejna

(74) *Attorney, Agent, or Firm* — Scully, Scott, Murphy & Presser, P.C.

(57) ABSTRACT

An endoscope clip including; first and second jaws pivotally connected together for movement between open and closed positions, and a spring biasing the first and second jaws into the closed position, wherein each of the first and second jaws comprise: a tube engaging portion, wherein opposing pairs of tube engaging portions for the first and second jaws define two or more adjacent channels configured to receive a portion of an endoscope tube, wherein each of the two or more adjacent channels has an arcuate longitudinal axis; and an actuation portion operable by a user to overcome the biasing action of the spring to open the first and second jaws.

10 Claims, 2 Drawing Sheets

(56) References Cited

U.S. PATENT DOCUMENTS

| | | | |
|---|---|---|---|
| 7,559,125 B2* | 7/2009 | Cofer | A61M 5/1418 24/500 |
| 8,869,355 B2* | 10/2014 | Huang | H02G 3/32 24/329 |
| 9,127,786 B1* | 9/2015 | Arratia | A61M 25/013 |
| 10,493,243 B1* | 12/2019 | Braham | A61M 25/02 |
| 10,556,058 B2* | 2/2020 | Tamrazi | A61M 25/02 |
| 10,813,439 B2* | 10/2020 | Huang | F16B 2/10 |
| 2007/0016135 A1* | 1/2007 | Kanner | A61M 5/46 604/117 |
| 2009/0247819 A1 | 10/2009 | Wilson et al. | |
| 2011/0049867 A1 | 3/2011 | Mori | |
| 2014/0073854 A1 | 3/2014 | Vincent et al. | |
| 2015/0238035 A1 | 8/2015 | Montgomery | |
| 2016/0074628 A1 | 3/2016 | Smith et al. | |
| 2017/0273716 A1 | 9/2017 | Garofalo et al. | |
| 2018/0049834 A1 | 2/2018 | Awadu | |
| 2018/0296066 A1 | 10/2018 | Kinoshita et al. | |
| 2019/0262577 A1 | 8/2019 | Anderson | |
| 2019/0346643 A1 | 11/2019 | Chu | |

\* cited by examiner

ENDOSCOPE CLIP

CROSS-REFERENCE TO RELATED APPLICATION

The present application is based upon and claims the benefit of priority from GB 2018979.1 filed on Dec. 2, 2020, the entire contents of which is incorporated herein by reference.

BACKGROUND

Field The present disclosure relates to an endoscope clip for holding an endoscope in a coiled configuration.

Prior Art

Endoscopes are long, flexible, tubular instruments which are used in the medical field for viewing inside a patient's body. Endoscopes are also used in an industrial context for inspecting inside complex machinery or equipment which is difficult to access. The main part of an endoscope is often referred to as the insertion tube. This usually contains multiple channels, e.g., for steering elements, biopsy equipment and supplying irrigation fluid, and numerous components which may be optical, mechanical and electrical. Therefore, an endoscope must be handled carefully to avoid damage and, in a medical environment in particular, it must be kept clean.

For gastrointestinal (GI) procedures, an endoscope insertion tube may be in the order of 1.5-2.5 m long, with a diameter in the order of 9-11 mm Before and after an endoscopy procedure, the endoscope is often draped over a hook or other piece of equipment but due to its length it may need to be hung at a very high level which is not accessible to all staff, to ensure that it does not touch the floor. Thus, given the length of the endoscope it can be difficult to handle and to temporarily store it safely and in a compact manner

SUMMARY

Accordingly, an endoscope clip is provided. The endoscope clip comprising first and second jaws pivotally connected together for movement between open and closed positions, and a spring biasing the jaws into the closed position, wherein each jaw comprises a tube engaging portion and an actuation portion operable by a user to overcome the biasing action of the spring in order to open the jaws, and each tube engaging portion defines two or more adjacent channels configured to receive a portion of an endoscope tube, wherein each channel has an arcuate longitudinal axis.

This configuration of clip can securely hold an endoscope in a coiled configuration without damage to the endoscope.

The surface of each channel can be curved in a plane transverse to the longitudinal axis, to conform to part of the outer surface of an endoscope insertion tube. Each channel may be dimensioned to fit an endoscope tube with an outer diameter of approximately 9-11 mm.

Each actuation portion can comprise an arm projecting from the tube engaging portion where the spring is located between the arms.

In one embodiment, the minimum radius of curvature of the arcuate longitudinal axis channels may be in the range of 200-250 mm, and the length of each channel along the longitudinal axis may be in the range of 5-10 cm.

The surface of each channel may be textured to enhance its grip on an endoscope tube. Similarly, an exterior surface of the actuation portions of each jaw can be textured to enhance a user's grip. The clip may further comprise a hook on at least one jaw configured to hang the clip on another item of equipment.

BRIEF DESCRIPTION OF THE DRAWINGS

The embodiments will now be described in detail, by way of example only, with reference to the accompanying drawings in which.

DETAILED DESCRIPTION

Figure 1:
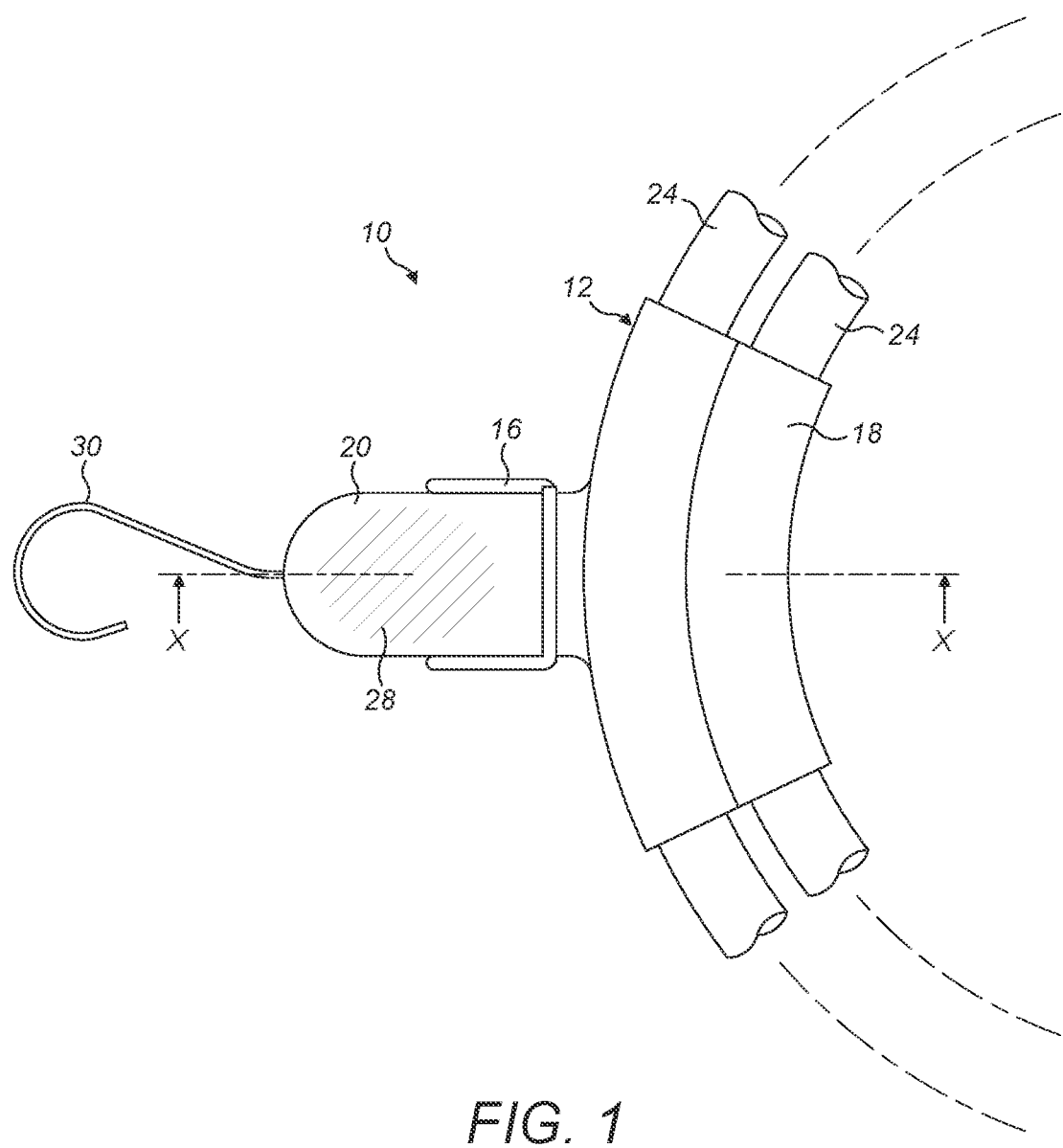
FIG. 1 illustrates a plan view of an endoscope clip.

An endoscope clip 10 comprises first and second jaws 12, 14, which are pivotally connected together for movement between closed and open positions. The jaws 12, 14 are biased into the closed position by a spring 16.

Each jaw 12, 14 comprises a tube engaging portion 18 and an actuation portion 20. In use, portions of an endoscope insertion tube 24 can be held between the tube engaging portions 18 of the first and second jaws 12, 14. The jaws 12, 14 grip the endoscope due to the biasing action of the spring 16. The user can operate the actuation portion 20 of the jaws 12, 14 in order to open the clip 10 to allow the endoscope to be inserted or removed from the clip 10.

Figure 2:
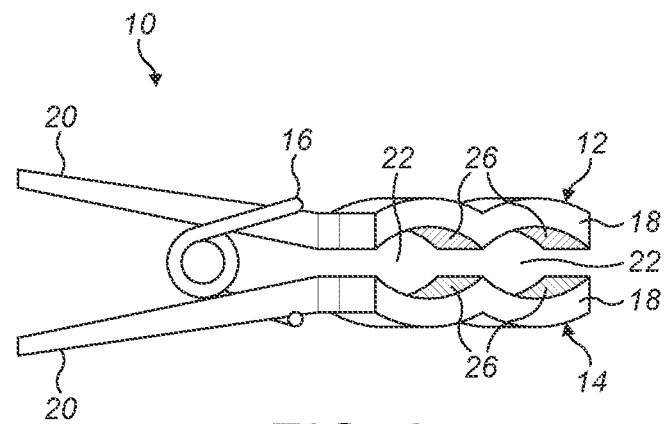
FIG. 2 illustrates a side view of the clip of FIG. 1 in the closed position.
Figure 3:
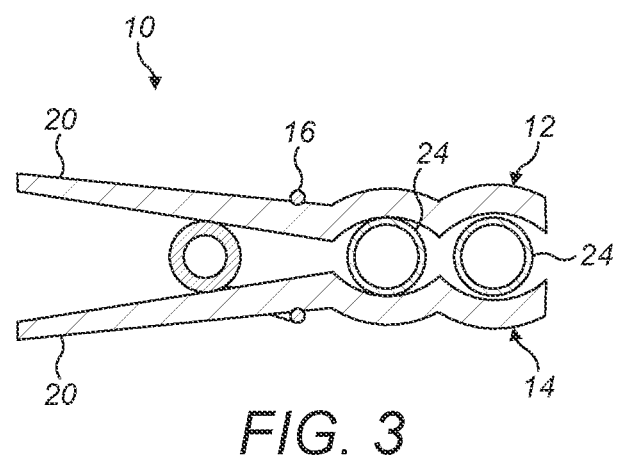
FIG. 3 illustrates a cross section along the line XX of FIG. 1 showing the clip holding an endoscope tube.

FIG. 1 shows a plan view of the endoscope clip 10, showing the first jaw 12. The second jaw 14 is identical and thus an underneath view of the clip 10 would be the same. The tube engaging portion 18 is arcuate. As shown in FIGS. 2 and 3, the interior surface of the tube engaging portion 18, that is the surface facing the other jaw, is shaped in order to define two adjacent channels 22 between the jaws 12, 14 each configured to receive a turn of a coiled endoscope.

Each channel 22 in the plan view has a curved longitudinal axis defined by a radius of curvature which is at least the minimum radius of curvature acceptable for a coiled endoscope which will not cause any damage to the internal components of the endoscope. For a typical GI endoscope, the minimum radius of curvature may be in the order of 200-250 mm.

As shown in FIGS. 2 and 3, the surface of each channel 22 is also curved in a cross-sectional plane transverse to the longitudinal axis. Thus, each channel 22 has a shape which will conform to part of the outer surface of an endoscope insertion tube. For example, the channels 22 may be dimensioned to fit an endoscope tube with an outer diameter of approximately 9-11 mm.

The clip 10 can have two channels 22 in each jaw 12, 14 and thus can hold two turns of a coiled endoscope. However, larger jaws 12, 14 with more than two adjacent channels 22 could be provided if required.

The actuation portion 20 of each jaw 12, 14 comprises an arm extending from the radially outer edge of the tube engaging portion 18. The actuation portions 20 can be flat and arranged for a user to grip between a finger and thumb in order to open the clip 10 against the biasing action of the spring 16.

The spring 16 is located between the two actuation portions 20 and may be of any convenient type. Numerous examples of suitable springs will be well known to a person skilled in the art. For example, the spring 16 may be similar to that found on a clothes peg, with a helical coil located between the two actuation portions 20, and an extension from each end of the coil connected to each jaw 12, 14. Alternatively, a coil spring or a leaf spring may be fitted between the two actuation portions 20.

In use, a user squeezes the two actuation portions 20 towards each other, against the action of the spring 16, which causes the tube engaging portions 18 to move further away from each other, opening the jaws 12, 14. Adjacent turns of a coiled endoscope insertion tube 24 can then be placed within the jaws 12, 14, locating in the channels 22 as shown. When the user no longer squeezes the actuation portions 20, the spring 16 acts to bias the jaws 12,14 back towards the closed position to grip the tubes 24.

The interior surface 26 of the channels 22 may be textured or provided with an additional coating to enhance their grip upon the external surface of an endoscope, or to provide cushioning to protect the endoscope. Similarly, the external surface of the actuation tabs 20 may also be provided with features to enhance a user's grip.

The clip 10 may also be provided with a hook, for example projecting from one of the actuation arms 20, allowing the clip 10 and a coiled endoscope that is holding to be hung on another item of equipment.

The size of the clip 10 can be adjusted to suit a desired type of endoscope. For example, for use with a GI endoscope, the length of the channels 22 along the longitudinal axis may be in the region of 5-10 cm. The radius of curvature of the longitudinal axis may be in the region of 200-250 mm.

The clip 10 can be formed with jaws 12, 14 made of plastic, and with the spring 16 made of metal.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope clip comprising;
    first and second jaws pivotally connected together about a pivot axis for movement between open and closed positions, and
    a spring biasing the first and second jaws into the closed position,
    wherein each of the first and second jaws comprise:
        an arcuate tube engaging portion having a radially inward side and a radially outward side, wherein opposing pairs of tube engaging portions for the first and second jaws define two or more adjacent channels configured to receive a portion of an endoscope tube, wherein each of the two or more adjacent channels has an arcuate longitudinal axis; wherein a first channel of the two or more adjacent channels having a first arc length is located on the radially inward side and a second channel of the two or more adjacent channels having a second arc length larger than the first arc length is located on the radially outward side; and the arcuate longitudinal axis of each of the first and second channels and the pivot axis all lie in the same plane; and
    a lever arm operable by a user to overcome the biasing action of the spring to open the first and second jaws, wherein the lever arm of each of the first and second jaws and the pivot axis are located on a radially outer side of the tube engaging portion, the lever arm of each of the first and second jaws being fixed to the radially outward side of a respective arcuate tube engaging portion.

2. An endoscope clip as claimed in claim 1, wherein a surface of each of the two or more adjacent channels is curved in a plane transverse to the longitudinal axis.

3. An endoscope clip as claimed in claim 2, wherein each of the two or more adjacent channels is dimensioned to fit an endoscope tube with an outer diameter of approximately 9-11 mm.

4. An endoscope clip as claimed in claim 1, wherein the first and second lever arms projecting from the first and second jaws, respectively, and the spring is located between the first and second lever arms.

5. An endoscope clip as claimed in claim 1, wherein the arcuate longitudinal axis is curved with a minimum radius of curvature in a range of 200-250 mm.

6. An endoscope clip as claimed in claim 1, wherein the first arc length and the second arc length are in a range of 5-10 cm.

7. An endoscope clip as claimed in claim 1, wherein a surface of each of the two or more adjacent channels is textured to enhance its grip on the endoscope tube.

8. An endoscope clip as claimed in claim 1, wherein the surface of each of the two or more adjacent channels comprises a cushioning to protect the endoscope tube.

9. An endoscope clip as claimed in claim 1, wherein an exterior surface of the first and second lever arms are textured to enhance a user's grip.

10. An endoscope clip as claimed in claim 1, further comprising a hook on at least one of the first and second jaws, the hook being configured to hang the clip on another item of equipment.

* * * * *